US008062860B2

(12) United States Patent
Dertinger (10) Patent No.: US 8,062,860 B2
(45) Date of Patent: Nov. 22, 2011

(54) KIT FOR MEASURING IN VIVO MUTATION FREQUENCY AT AN ENDOGENOUS GENE LOCUS

(75) Inventor: Stephen D. Dertinger, Webster, NY (US)

(73) Assignee: Litron Laboratories, Ltd., Rochester, NY (US)

( * ) Notice: Subject to any disclaimer, the term of this patent is extended or adjusted under 35 U.S.C. 154(b) by 0 days.

(21) Appl. No.: 12/899,217

(22) Filed: Oct. 6, 2010

(65) Prior Publication Data

US 2011/0027793 A1 Feb. 3, 2011

Related U.S. Application Data

(62) Division of application No. 11/752,726, filed on May 23, 2007, now Pat. No. 7,824,874.

(60) Provisional application No. 60/808,445, filed on May 25, 2006.

(51) Int. Cl.
*G01N 31/22* (2006.01)
*G01N 1/00* (2006.01)
*G01N 21/64* (2006.01)
*G01N 33/00* (2006.01)

(52) U.S. Cl. .................. 435/7.25; 435/7.21; 435/287.2; 435/334; 435/355; 435/973; 436/521; 436/522; 436/10; 436/17; 436/63; 436/94; 436/172; 436/175; 436/811; 422/73; 422/82.08; 422/430; 424/9.2

(58) Field of Classification Search .............. 435/7.21, 435/7.23, 7.24, 7.25, 287.2, 334, 355, 973; 436/521, 522, 536, 548, 10, 17, 63, 64, 94, 436/172, 175, 177, 811; 422/73, 82.05, 82.08, 422/430; 424/9.2
See application file for complete search history.

(56) References Cited

U.S. PATENT DOCUMENTS

| 4,444,879 | A  | * | 4/1984 | Foster et al. ................. 435/7.95 |
| 5,314,805 | A  |   | 5/1994 | Haugland et al. |
| 5,858,667 | A  |   | 1/1999 | Dertinger et al. |
| 6,100,038 | A  |   | 8/2000 | Dertinger et al. |
| 6,593,095 | B1 | * | 7/2003 | Buckley et al. ............. 435/7.24 |
| 7,358,059 | B2 | * | 4/2008 | Orfao De Matos Correia E Vale ............................ 435/7.21 |
| 2003/0138851 | A1 | | 7/2003 | De Matos et al. |
| 2005/0042602 | A1 | | 2/2005 | Ahearn et al. |
| 2006/0040291 | A1 | | 2/2006 | Dertinger et al. |

(Continued)

OTHER PUBLICATIONS

Ware et al., Immunophenotypic Analysis of Reticulocytes in Paroxysmal Nocturnal Hemoglobinuria, Blood 86 (4): 1586-1589 (Aug. 15, 1995).*

(Continued)

*Primary Examiner* — Gail R Gabel
(74) *Attorney, Agent, or Firm* — LeClairRyan, a Professional Corporation (57) ABSTRACT

The present invention relates a method for the enumeration of in vivo gene mutation. The method utilizes differential staining of GPI-anchor deficient erythrocyte populations to distinguish between wild-type and pig-a gene mutants. Quantitative analyses can be conducted on erythrocytes and/or reticulocytes, and is based upon fluorescent emission and light scatter following exposure to an excitatory light source. Counting of mutant erythrocytes or reticulocytes relative to the number of total erythrocytes or reticulocytes can be used to assess the DNA-damaging potential of an exogenous chemical agent, the DNA-damaging potential of an exogenous physical agent, the effects of an exogenous agent which can modify endogenously-induced DNA damage, and the effects of an exogenous agent which can modify exogenously-induced DNA damage. Kits for practicing the invention are also disclosed.

21 Claims, 7 Drawing Sheets

U.S. PATENT DOCUMENTS

2006/0140963 A1* 6/2006 Young et al. .............. 424/155.1
2007/0274919 A1 11/2007 Dertinger
2009/0311706 A1* 12/2009 Dertinger .......................... 435/6

OTHER PUBLICATIONS

Albertini, "Somatic Mutation Models of Relevance for Humans," Environmental Mutagen Society, Meeting Abstracts, No. 8 (p. 161) (May 2003).

Miura et al., "Development of an In Vivo Gene Mutation Assay Using the Endogenous Pig-A Gene: I. Flow Cytometric Detection of CD59-Negative Peripheral Red Blood Cells and CD48-Negative Spleen T-Cells from the Rat," Environ. Mol. Mutagen 49:614-621 (2008).

Hernandez-Compo et al., "Quantitative Analysis of the Expression of Glycosylphosphatidylinositol-Anchored Proteins During the Maturation of Different Hematopoietic Cell Compartments of Normal Bone Marrow," Cytometry Part B (Clin. Cytometry) 72B:34-42 (2007).

Chen et al., "Glycophosphatidylinositol-Anchored Protein Deficiency as a Marker of Mutator Phenotypes in Cancer," Cancer Res. 61:654-658 (2001).

Wang et al., "Clinical Significance of a Minor Population of Paroxysmal Nocturnal Hemoglobinuria-Type Cells in Bone Marrow Failure Syndrome," Blood 100(12):3897-3902 (2002).

Ware et al., "Immunophenotypic Analysis of Reticulocytes in Paroxysmal Nocturnal Hemoglobinuria," Blood 86 (4):1586-1589 (1995).

Araten et al., "A Quantitative Measurement of the Human Somatic Mutation Rate," Cancer Res. 65(18):8111-8117 (2005).

Ware, Russell E., "Is There a Little PNH in All of Us?," Blood 105(10):3760-3761 (2005).

Hernandez-Campo et al., "Comparative Analysis of Different Flow Cytometry-Based Immunophenotypic Methods for the Analysis of CD59 and CD55 Expression on Major Peripheral Blood Cell Subsets," Cytometry (Clin. Cytometry) 50:191-201 (2002).

Parker et al., "Diagnosis and Management of Paroxysmal Nocturnal Hemoglobinuria," Blood 106(12):3699-3709 (2005).

Bryce et al., "In vivo Mutation Assay Based on the Endogenous Pig-a Locus," Environ. Mol. Mutagen 49(4):256-264 (2008).

\* cited by examiner

KIT FOR MEASURING IN VIVO MUTATION FREQUENCY AT AN ENDOGENOUS GENE LOCUS

This application is a divisional of U.S. patent application Ser. No. 11/752,726, filed May 23, 2007, now U.S. Pat. No. 7,824,874, which claims the priority benefit of provisional U.S. patent application Ser. No. 60/808,445, filed May 25, 2006, each of which is hereby incorporated by reference in its entirety.

This work was supported by a grant from the National Cancer Institute under grant number R43 CA106063. The U.S. government retains certain rights in this invention.

FIELD OF THE INVENTION

This invention relates to an analytical method for measuring the in vivo mutation frequency caused by an exogenous agent to which a mammal has been exposed, either intentionally or unintentionally.

BACKGROUND OF THE INVENTION

DNA damage can result in mutation, and this is a primary mechanism by which cancers arise. These events have also been implicated in diseases such as atherosclerosis, and processes such as aging. Therefore, there is an important need for sensitive methods which are capable of identifying chemical or physical agents that can mutate DNA. Given the tremendous cost of long-term chronic studies such as 2-year carcinogenicity tests, short- and medium-term systems for predicting DNA reactivity play a vital role in tumorigenic agent identification.

Although sensitive assays for measuring in vitro mutation exist (e.g., Salmonella reverse mutation test, mouse lymphoma forward mutation assay), in vivo methods are needed to form a more complete understanding of risk. Thus, while there are National Institutes of Health (NIH) directives to reduce animal usage for toxicity testing purposes, it is well appreciated that whole animal systems are necessary for faithful incorporation of variables such as toxicant deposition, metabolism, and elimination. Because the in vivo system proposed herein is based on blood sampling and therefore does not require sacrifice, it can easily be integrated into on-going acute, subacute, or subchronic toxicology studies. This approach would help minimize animal usage, as the number of dedicated experiments conducted to assess genotoxicity is reduced. Furthermore, since it should be possible to extend the method beyond laboratory rodents to man, it could play an important role in studying new drugs during clinical trials, or for myriad other human biomonitoring applications.

Some of the more widely utilized assays for studying in vivo mutation are listed in Table I below along with the assay of the present invention. While some are based on colony formation and therefore require time-consuming tissue culture work after target cells have been harvested, others require expensive breeding programs to supply rodents with a specific genotype.

TABLE I

Overview of in vivo Mutation Assays

| Target Gene | Special Requirements | Target Cells | Culture Work | Enumeration |
|---|---|---|---|---|
| hprt | Compatible with all mammals | Blood (or spleen) lymphocytes | Yes | Colony formation |
| thymidine kinase | Requires tk+/− mice | Blood (or spleen) lymphocytes | Yes | Colony formation |
| Glycophorin A | Heterozygous humans (M-N blood antigens) | Blood RBCs | No | Flow cytometry |
| Transgenic lacZ or lacI | Proprietary rodents (e.g., Muta ™ Mouse, BigBlue ® Mouse or Rat) | Any | Yes (bacteria and phage) | Plaque formation |
| pig-a* | Compatible with all mammals | Blood RBCs (and other blood cells) | No | Flow cytometry |

Abbreviations:
hprt = hypoxanthine phosphorylribosyl transferase;
tk+/− = thymidine kinase heterozygote
*pig-a is the target of the present invention; it is compared here based on the manner of detection described in the present application.

As Table I suggests, the invention described herein is not the first to quantitatively measure in vivo mutation. The novelty and advantages of the present invention stem from careful attention to the choice of gene locus and the target cells. Importantly, these mutation data will be available without the need for time and resource-intensive tissue culture work, or the use of costly transgenic animals. Furthermore, given the compatibility of enumerating the mutant phenotype via flow cytometric analysis, the assay of the present invention is endowed with a high throughput capacity. The methodology of the present invention has other advantages relative to the current state-of-the-art. These advantages include: compatibility with any mammalian species, easy integration into other studies, and conceivably higher relevance for the reporter gene, which is endogenous and transcribed (as compared to transgenes which are non-transcribed, have high G-C content, and are extensively methylated).

Figure 1:
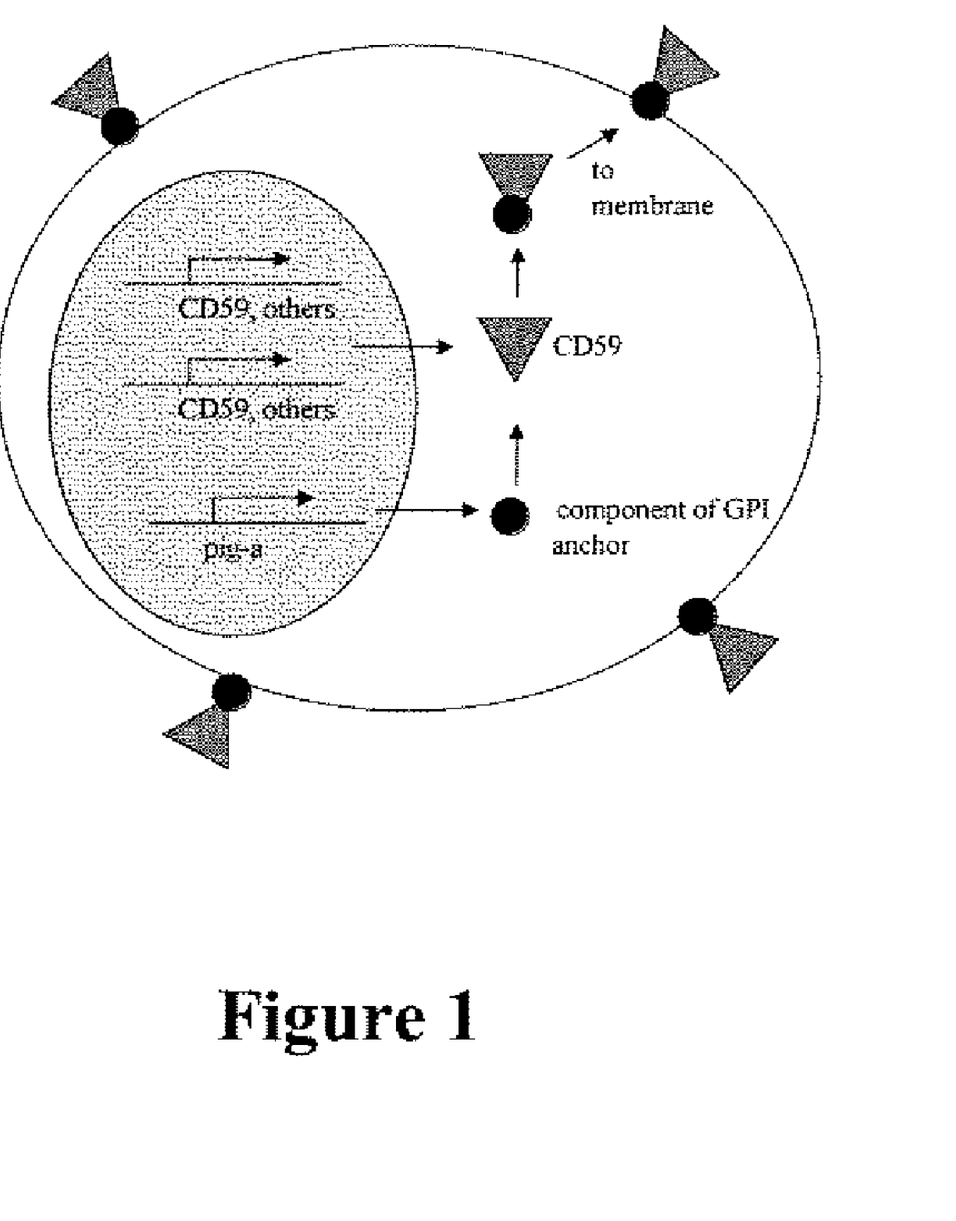

The pig-a gene is located on the X-chromosome. This is a highly desirable feature, since one functional copy means that only a single mutational event is necessary to produce a phenotype which can be readily detected. More specifically, the pig-a gene product is essential for the biosynthesis of glycosyl-phosphatidylinositol (GPI) anchors. Mutations giving rise to non-functional pig-a product result in the absence or the reduced membrane expression of GPI-linked proteins in peripheral blood cells. See FIG. 1.

Paroxysmal Nocturnal Hemoglobinuria (PNH) is a genetic disorder that affects 1 to 10 per million individuals. The molecular basis of PNH is a somatic pig-a gene mutation within a bone marrow stem cell. PNH usually affects erythrocytes, granulocytes and monocytes. Occasionally, only the erythrocytes, or the granulocytes and monocytes, are affected. In a minority of cases the lymphocyte lineage is also affected, and only a few rare case reports have documented the lymphocytes to be the only cell lineage affected. Several GPI-linked proteins, especially CD59 and CD55, have been studied intensely. In fact, flow cytometry-based techniques which measure the frequency of CD59 and/or CD55 deficient red blood cells are replacing the traditional HAM test for PNH diagnosis. Even so, it is important to recognize that since clinically significant disease requires a relatively large fraction of cells to exhibit GPI-anchor deficiency, these PNH diagnostic assays have not required the degree of accuracy that a rare-event/mutation scoring system will require. Thus, the repurposing of pig-a gene mutation measurements for evaluating genotoxicity, as opposed to diagnosing PNH disease, requires the high throughput and reliability characteristics of the present invention.

The present invention is directed to overcoming these and other deficiencies in the art.

SUMMARY OF THE INVENTION

A first aspect of the present invention relates to a method for the enumeration of in vivo pig-a gene locus mutation. This method includes the steps of: providing a blood or bone marrow sample from a mammal exposed to an exogenous agent, the blood or bone marrow sample comprising erythrocytes and reticulocytes; first contacting the sample with a first reagent that binds GPI-anchor-expressing erythrocytes and reticulocytes, but not GPI-anchor-deficient erythrocytes and reticulocytes, and that is conjugated to or can be bound by a first fluorochrome; second contacting the sample with a second reagent that binds to mammalian platelets, and that is conjugated to or can be bound by a second fluorochrome having a fluorescent emission spectrum that does not substantially overlap with a fluorescent emission spectrum of the first fluorochrome; third contacting the sample with a third fluorochrome-containing reagent that labels reticulocytes but not mature erythrocytes, the third fluorochrome having a fluorescent emission spectrum that does not substantially overlap with the fluorescent emission spectra of the first and second fluorochromes; exciting the first, second, and third fluorochromes with light of appropriate excitation wavelength; and detecting the fluorescent emission and light scatter produced by erythrocytes and reticulocytes labeled with the first fluorochrome, while excluding platelets labeled by the second fluorochrome and nucleated cells (reticulocytes vs. mature erythrocytes) labeled by the third fluorochrome, and counting the number of GPI-anchor deficient erythrocytes and/or reticulocytes relative to the number of total erythrocytes or reticulocytes. The number of GPI-anchor deficient erythrocytes and/or reticulocytes relative to the number of total erythrocytes or reticulocytes represents the pig-a mutation frequency. When compared to a baseline frequency (i.e., an average spontaneous pig-a mutation frequency), the effects of the exogenous agent on the pig-a mutation frequency can be assessed.

A second aspect of the present invention relates to a method of assessing the DNA-damaging potential of an exogenous chemical agent. This method includes the steps of: exposing a mammal to an exogenous chemical agent, and performing the method according to the first aspect of the present invention, wherein a significant deviation in the frequency of GPI-anchor-deficient erythrocytes or reticulocytes from a baseline GPI-anchor-deficient erythrocyte or reticulocyte frequency in unexposed or vehicle control mammals indicates the genotoxic potential of the exogenous chemical agent A third aspect of the present invention relates to method of assessing the DNA-damaging potential of an exogenous physical agent. This method includes the steps of: exposing a mammal to an exogenous physical agent, and performing the method according to the first aspect of the present invention, wherein a significant deviation in the frequency of GPI-anchor-deficient erythrocytes or reticulocytes from a baseline GPI-anchor-deficient erythrocytes or reticulocyte frequency in unexposed or sham-exposed control mammals indicates the genotoxic potential of the exogenous physical agent.

A fourth aspect of the present invention relates to a method of evaluating the effects of an exogenous agent that can modify endogenously-induced DNA damage. This method includes the steps of: administering to a mammal an exogenous agent that may modify endogenously-induced genetic damage; and performing the flow cytometric method according to the first aspect of the present invention, wherein a significant deviation in the frequency of GPI-anchor-deficient erythrocytes or reticulocytes from a baseline GPI-anchor-deficient erythrocytes or reticulocyte frequency indicates that the exogenous agent can modify endogenous DNA damage.

A fifth aspect of the present invention relates to a method of evaluating the effects of an exogenous agent that can modify exogenously-induced DNA damage. This method includes the steps of administering to a mammal a first exogenous agent that may modify exogenously-induced genetic damage; exposing the mammals to an second exogenous agent that causes genetic damage; and then performing the flow cytometric method according to the first aspect of the present invention, wherein a significant deviation in the frequency of GPI-anchor-deficient erythrocytes or reticulocytes for genotoxicant-exposed mammals indicates that the first exogenous agent can modify exogenously-induced DNA damage.

A sixth aspect of the present invention relates to a kit that includes: a first reagent that binds GPI-anchor-expressing cells, but not GPI-anchor-deficient cells, and that is conjugated to or can be bound by a first fluorochrome; a second reagent that binds to mammalian platelets, and that is conjugated to or can be bound by a second fluorochrome having a fluorescent emission spectrum that does not substantially overlap with a fluorescent emission spectrum of the first fluorochrome; a nucleic acid dye that has a fluorescent emission spectrum that does not substantially overlap with the fluorescent emission spectra of the first and second fluorochromes; and, optionally, one or more balanced salt solutions.

The present invention identifies procedures that can be employed for an automated in vivo mutation assay that can be used to evaluate agents (e.g., chemical or physical agents) for genetic toxicity. It can also be used to assess the magnitude and/or consequences of occupational, accidental, other unintentional exposure scenarios. The procedure is fast, reliable, and accurate, and can be performed without the need for transgenic animal models or cell culture work.

BRIEF DESCRIPTION OF THE DRAWINGS

FIG. 1 is a schematic of a cell showing expression of CD59 and pig-a gene products. Since the gene that encodes CD59 and other GPI-anchored proteins exist on each of two alleles, it would take two independent mutational events to prevent the cell surface expression of any one of these antigens. In contrast, a single mutational event at the pig-a gene (X-chromosome) has the potential to interfere with cell surface expression of all GPI-anchored proteins. Lack of expression of one or more GPI-anchored proteins is a phenotype that can be measured by flow cytometry using appropriate antibodies or a fluorescent derivative of the toxin aerolysin.

FIG. 3A illustrates the Light Scatter plot; events must be within the "Single Cells" region. FIG. 3B illustrates the ability of the nucleic acid dye Thiazole Orange (X-axis) to distinguish mature erythrocytes, reticulocytes, and nucleated cells, while anti-CD61-Cy-PE (Y-axis) labels platelets. In this example, only events within the region "Total RBCs" are evaluated for CD59 expression. FIG. 3C illustrates the anti-CD59-PE fluorescence vs. Forward Scatter for a rat blood specimen. This plot shows events within the "Single Cells" region, without consideration of Thiazole Orange or anti-platelet antibody-associated fluorescence. This limited gating strategy results in contamination of the region intended for mutant RBC scoring by nucleated cells and to a lesser extent platelets. FIG. 3D illustrates the same negative control rat data as shown in FIG. 3C, but with events gated on the "Single Cells" and "Total RBCs" regions. Having eliminated nucleated cells and platelets based on Thiazole Orange and anti-platelet antibody-associated fluorescence, reliable enumeration of mutant and wild type erythrocytes is possible. The relative rarity of mutant (CD59-negative) RBCs is readily apparent for this vehicle control animal. FIG. 3E illustrates data obtained from an ethyl-N-nitrosourea-treated rat, with events gated on the "Single Cells" and "Total RBCs" regions. The relatively high frequency of mutant erythrocytes for this genotoxicant-treated animal is apparent.

FIGS. 4A-B are bivariate graphs which illustrate analyses based on FSC thresholding (left), and FL1 thresholding (right). FSC thresholding is capable of efficiently acquiring mutation frequency data for the total RBC population, but it does not allow for rapid interrogation of reticulocytes. The plot on the right was generated using FL1 thresholding (thiazole orange intensity). This strategy allowed the application of high density samples to the flow cytometer, while "ignoring" mature erythrocytes and greatly improving reticulocyte throughput.

DETAILED DESCRIPTION OF THE INVENTION

The present invention is directed to a method for the measurement of pig-a mutant erythrocyte and/or pig-a mutant reticulocyte frequencies using an optical device designed for illumination and analysis of cell specimens.

For purposes of the present invention, erythrocytes is intended to mean enucleated red blood cells, regardless of RNA or CD71-antigen expression levels. For the purposes of the present invention, reticulocytes is intended to mean recently formed enucleated red blood cells, characterized by the presence of cytoplasmic RNA, and/or the expression of the cell surface antigen CD71. For the purposes of the present invention, pig-a mutant cells is intended to mean erythrocytes and/or reticulocytes with altered pig-a DNA sequence, such that transcription of the pig-a gene is affected, resulting in a phenotype which is distinguishable by either a lack of or significant deficiency of GPI-anchored proteins on the cell surface. For the purposes of this invention, expression time is intended to mean the period of time following exposure of a DNA damaging event until the time that a mutated cell both expresses the GPI-anchor deficient phenotype and also appears in peripheral blood circulation.

The invention described herein provides for the measurement of pig-a mutant frequency, preferably using flow cytometry technology. The advantageous characteristics of this invention relative to other in vivo mutation assays which have been reported to date are that it does not require transgenic animals, special breeding programs, or cell culture; and it is compatible with all mammalian species. Other advantages will become apparent in the discussion of the various embodiments.

With this method, blood specimens are obtained from mammals. If the exposure that one wishes to evaluate is acute, then a period of expression time is allowed to occur before samples are collected into an anticoagulant solution according to standard practices. If the exposure that one wishes to evaluate has been repeated and protracted, for instance as occurs for subchronic or chronic toxicity tests, then it will usually not be necessary to allow for a period of expression time before blood samples are collected. Alternatively, multiple samples can be collected over a period of time to monitor such longterm exposure.

Erythrocytes are either separated from the other blood components according to standard practices, or else whole blood is centrifuged one or more times and the cell pellet resuspended in a balanced salt solution.

To achieve pig-a mutant cell scoring according to the present invention, washed and fractionated erythrocytes or washed unfractionated blood cells are incubated with a reagent that binds to GPI-anchor competent (wild-type) cells, but not GPI-anchor deficient (pig-a mutant) cells. By using a reagent that is either directly conjugated to a first fluorochrome, or else one that can be readily bound to a subsequently applied first fluorochrome, differential labeling of wild-type and mutant cells is achieved. Ideally, the specificity of the interaction is high, for instance that which is typically found with antibody-antigen interactions.

Preferred antibodies include, without limitation, first fluorochrome-conjugated anti-CD55 and/or anti-CD59 antibodies, or a combination thereof. Alternatively, anti-CD55 and/or anti-CD59 antibodies can be used in combination with secondary antibodies labeled with a first fluorochrome.

Alternately, the high affinity and specificity of the bacterial toxin aerolysin for the GPI anchor can also be used as a basis for differentially labeling wild-type and pig-a mutant cells. For instance, a preferred embodiment includes contacting cells with a derivative of proaerolysin that binds to GPI anchors with high affinity, but does not lyse erythrocytes. This reagent is commercially available in a form that has been directly conjugated to a fluorochrome (FLAER™, available from Pinewood Scientific Services, Inc., Victoria, British Columbia), thus providing for direct labeling. Alternately, it is available as a biotinylated form (also from Pinewood), which provides for subsequent labeling with fluorochrome-conjugated avidin or streptavidin.

Subsequent to or concurrent with differential labeling of mutant and wild-type cells, a second reagent is added. The second reagent is one that specifically binds platelets (which may interfere with pig-a mutant cell scoring). By using a reagent that is either directly conjugated to a second fluorochrome, or else one that can be readily bound to a subsequently applied second fluorochrome, differential labeling of erythrocytes and platelets can be achieved.

Exemplary second reagents include, without limitation, second fluorochrome-conjugated anti-CD61 and/or anti-CD42b antibodies. Alternatively, anti-CD61 and/or anti-CD42b antibodies can be used in combination with secondary antibodies labeled with a second fluorochrome that is distinct of the first fluorochrome.

Subsequent to or concurrent with differential labeling of mutant versus wild-type cells, and platelets versus erythrocytes, the specimen is contacted with a third reagent. The third reagent is one that specifically binds to nucleic acids or the CD71 antigen (also known as the transferrin receptor). By using a fluorescent reagent, or one that can be readily bound to a subsequently applied third fluorochrome, differential labeling of reticulocytes from more mature erythrocytes is achieved.

Exemplary third reagents include, without limitation, the nucleic acid dyes thiazole orange, SYTO® 13 dye, SYTO® 83 dye, and SYTO® RNASelect™ (all of which are cyanine dyes available from Invitrogen Corporation, Carlsbad, Calif.), and third fluorochrome-conjugated anti-CD71 antibodies. Alternatively, anti-CD71 antibodies can be used in combination with secondary antibodies labeled with a third fluorochrome that is distinct of the first and second fluorochromes.

While immunodetection reagents are described for use in the methods of the present invention, it should be appreciated that any suitable immunolabel can be used, including without limitation monoclonal antibodies, polyclonal antibodies, mono-specific polyclonal antibody preparations, chimeric antibodies, single chain antibodies, synthetic antibodies, and any antibody fragments, e.g., Fab fragments, Fab' fragments, F(ab)$_2$ fragments, F(ab')$_2$ fragments, Fd fragments, Fv fragments, dAb fragments, and isolated complementarity determining regions ("CDRs") (see U.S. Pat. Nos. 7,037,498, 7,034,121, 7,041,870, and 7,074,405, which are hereby incorporated by reference in their entirety). These antibody fragments can be made by conventional procedures, such as proteolytic fragmentation procedures, as described in J. Goding, *Monoclonal Antibodies: Principles and Practice*, pp. 98-118 (N.Y. Academic Press 1983), which is hereby incorporated by reference in its entirety. Methods for preparing antibodies that are specific to an analyte of interest are well known in the art. Conjugation of desired fluorochromes to antibodies is also well known in the art, and such immunoreagents are commercially available.

The various fluorochromes and nucleic acid dyes should be selected such that they can all be excited by the one or more light sources, yet their emission spectra are sufficiently distinct. Preferably, the emission maxima of the various fluorchromes and nucleic acid dyes do not substantially overlap (i.e., they have distinct emission maxima). With regard to their excitation spectra, it is preferable for the reagents to have similar excitation spectra because that affords the use of the more widespread single-laser flow cytometer.

Samples that have been contacted with three fluorescent reagents as described should be stored at about 4° C. and protected from light until ready for analysis. In a preferred embodiment of the present invention, samples are analyzed on the same day as harvesting/staining.

Regardless of whether the samples are stored or treated the same day as harvested/stained, the treated sample can be subjected to optical detection and enumeration of pig-a mutant cells using any suitable optical detection system. Preferred optical detection systems have one or more light sources, preferably in the form of one or more amplified or collimated beams of light, that are able to excite the three fluorescent reagents. Exemplary optical detection systems include, without limitation, single-laser flow cytometers and dual- or multiple-laser flow cytometers.

Single-laser flow cytometric analysis uses a single focused laser beam with an appropriate emission band to excite the several fluorescent reagents. As stained cells pass through the focused laser beam, they exhibit a fluorescent emission maxima characteristic of the fluorochromes or dyes associated therewith. The flow cytometer is equipped with appropriate detection devices to enable detection of the fluorescent emissions and light scatter produced by the cells. In this way, cell populations are counted and the number of pig-a mutant erythrocytes and/or pig-a mutant reticulocytes can be ascertained.

Dual- or multiple-laser flow cytometric analysis use two or more focused laser beams with appropriate emission bands, in much the same manner as described above for the single-laser flow cytometer. Different emission bands afforded by the two or more lasers allow for additional combinations of fluorescent dyes or immunochemical-conjugated fluorochromes to be employed.

The low frequency of pig-a mutant cells in healthy mammals, for instance those that are untreated, sham-exposed or vehicle-treated, demands that a sensitive mutation scoring system be capable of interrogating at least several hundred cells per individual, but more ideally approximately $10^6$ cells per individual. This throughput is not particularly difficult when total erythrocytes are considered. However, there are at least two reasons to suggest there would be merit to performing pig-a mutation measurements in the reticulocyte fraction in addition to the total erythrocyte pool.

One advantage of reticulocyte-based measurements is suggested by work with the peripheral blood cells of PNH patients. It has been shown that the number of circulating GPI-deficient neutrophils is typically higher than the number of affected erythrocytes. One explanation for this finding is that PNH erythrocytes are subject to complement-mediated intravascular lysis. Therefore, it is possible that an analytical system that focuses on the newly formed reticulocytes would provide a more accurate mutation frequency. A report by Ware et al. supports this view (*Blood* 86:1586-1589 (1995), which is hereby incorporated by reference in its entirety). In their study, blood from 25 PNH patients was studied using flow cytometry. Thiazole orange was used to stain reticulocytes, and anti-CD59 was used to identify GPI-deficient cells. In contrast to the mature circulating erythrocytes, the percentage of abnormal reticulocytes was similar to the percentage of affected neutrophils. These data suggest that premature destruction of PNH erythrocytes may account for the fact that most patients have more GPI-deficient neutrophils than erythrocytes. Thus, a mutation assay based on reticulocytes may be more sensitive than one based on total erythrocytes, especially if mutant erythrocytes exhibit a shortened lifespan.

A second reason for studying pig-a mutation in reticulocytes is that this subpopulation would be expected to reflect genotoxicant-induced mutation more rapidly than the total erythrocyte pool. That is, mutation frequency in the reticulocyte population would be expected to be a "leading indicator" of genotoxicant exposure. This temporal relationship reflects the fact that the spontaneous mutant frequency can only be affected by genotoxicant exposure after a sufficient length of time has elapsed, one that allows for a significant fraction of pre-existing (low mutation frequency) cells to be replaced by cells that exhibit an elevated mutation frequency. The timeframe for turning over blood reticulocytes (days) is considerably shorter than for the total erythrocyte pool (several weeks to about 4 months, depending on species), and is consequently expected to provide a quickly responding cohort, versus one that lags in time. Thus, shortening of mutant cell expression time is therefore a second advantage for studying pig-a mutation in blood reticulocytes.

While rapid interrogation of reticulocytes is obviously desirable, their low incidence relative to total erythrocytes poses technical challenges. Despite the high throughput capacity of modern flow cytometers (often on the order of 7000 events per second), the interrogation of approximately $10^6$ reticulocytes for mutation is time consuming. At this rate, a whole blood specimen with 3% reticulocytes would require approximately 80 minutes to interrogate $10^6$ reticulocytes.

There are two solutions to this obstacle, both of which involve starting with very high density specimens. One is a so-called "thresholding technique", and the second a lysis procedure that entails selective lysis of cells. Both of these techniques were found to be effective, and these methods are taught in the examples provided herein.

The thresholding technique involves use of staining that distinguishes reticulocytes from mature erythrocytes (e.g., thiazole orange, SYTO 13 dye, SYTO 83 dye, RNASelect, or fluorochrome labeled anti-CD71 antibody). In addition, on the optical detection system, the threshold parameter is set for the nucleic acid dye-associated fluorescence channel (i.e., FL1 for thiazole orange) rather than the more common forward scatter trigger. When set sufficiently high (taking into consideration differences in fluorescence intensities between mature and immature erythrocytes owing to differential staining), this can eliminate the mature cells from analysis. Finally, the specimen to be processed should be of sufficiently high density so as to reduce the acquisition time. Preferably the cell density is at least about $1 \times 10^8$ cells/ml; higher cell densities can produce faster acquisition rates.

There are two lysis procedures that can be utilized. One involves the lysis of $GPI^+$ cells using the bacterial toxin aerolysin (or proaerolysin), while the other involves Complement-mediated lysis of anti-CD55 or anti-CD59 antibody-labeled $GPI^+$ cells.

The aerolysin procedure involves lysing $GPI^+$ cells with the bacterial toxin aerolysin. Aerolysin is one of the best characterized of the toxins secreted by pathogenic bacteria. It is released by *Aeromonas hydraphila* as an inactive 52-kDa precursor called proaerolysin, which is converted to aerolysin by proteolytic removal of a C-terminal peptide. Both aerolysin and proaerolysin are commercially available from Pinewood Scientific Services, Inc. (Victoria, British Columbia). Aerolysin targets several cell surface proteins, each of which has been shown to be GPI-anchored. This, together with many other observations, has proven that the anchor itself is the major aerolysin binding determinant. Toxin/GPI binding is known to promote oligomerization, which is rapidly followed by membrane insertion and channel formation. In the case of wild type erythrocytes, channel formation results in cellular lysis. Because pig-a mutants lose the capacity to form GPI anchors, they are resistant to aerolysin. This reagent therefore represents a powerful tool for enriching specimens for pig-a mutant cells.

The fact the erythrocyte ghosts resulting from aerolysin treatment cannot be directly counted by flow cytometry, each specimen to be analyzed is processed twice in conjunction with so called "counting beads". This strategy is graphically portrayed by FIG. 2.

Figure 2:
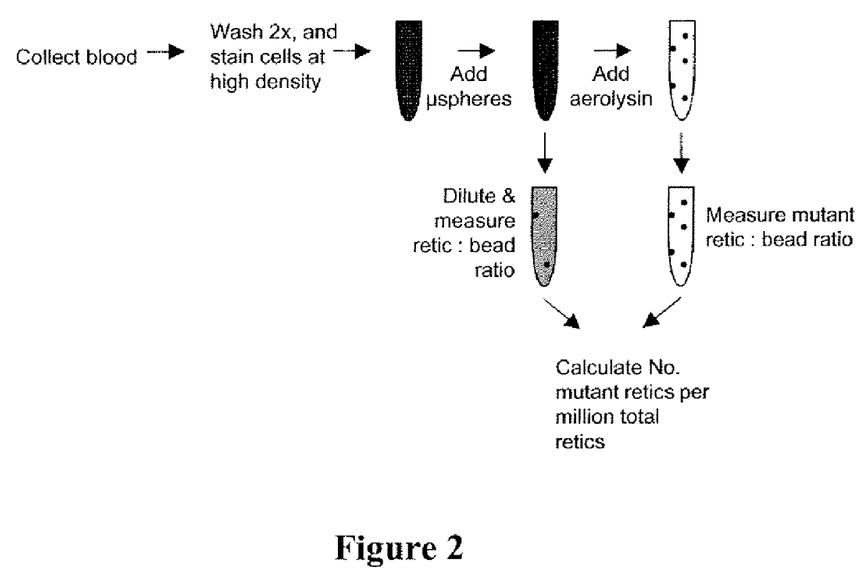
FIG. 2 is a schematic that illustrates the cell labeling and wild-type cell lysis strategy that affords rapid measurement of pig-a mutant reticulocyte frequency. A blood specimen is stained and resuspended at high density in a microsphere-containing buffer. One portion is diluted and the ratio of reticulocytes to beads is measured. The undiluted fraction is treated with aerolysin, and the ratio of surviving reticulocytes that are also CD59-negative is determined. The stop mode for this $2^{nd}$ analysis is the number of beads calculated to correspond to $10^6$ "virtual" total reticulocytes.

Blood samples are obtained and processed (labeling with fluorochromes) as described above. Specimens were subsequently divided to provide pig-a mutant erythrocyte frequency measurements made with and without the use of aerolysin. To each of the samples, a small volume of high density microsphere suspension is added. Preferably, between about $10^3$ to about $10^6$ microspheres/specimen are added. Suitable microspheres are commercially available from a number of sources, including Becton Dickinson, Molecular Probes, and Polysciences. After mixing each sample to ensure a homogeneous suspension, a small aliquot of each cell/microsphere solution is transferred to a tube containing a balanced salt solution such that the resulting dilution yields a density of beads and cells which is low enough so that the rate of particles passing through the detection device yields accurate measurements (e.g., less than about 7,000 events per second for a Becton Dickinson FACSCalibur; higher densities may lead to excessive coincidence, which is multiple particles simultaneously at the fluid stream-laser beam intersection). The other (undiluted) specimen is treated with aerolysin to lyse the majority of non-mutant erythrocytes and reticulocytes. Reticulocyte:bead ratios are measured for both diluted and undiluted/aerolysin-treated samples using, e.g., an optical detection system of the type described above. From these ratios, it is possible to calculate the frequency of mutant reticulocytes per $10^6$ reticulocytes.

For example, a small volume of a bead stock suspension (10 µl) is added to a suspension of high density cells that have been stained for a mutation frequency determination (1 ml). A small fraction of the cell/bead suspension is then transferred to a tube containing an isotonic solution such that the resulting density of beads and cells is low enough to prevent excessive coincidence. Flow cytometric analysis then allows for determination of the reticulocyte to bead ratio; for example 7,500 reticulocytes and 100 beads would indicate a ratio of 75 reticulocytes per bead. The aerolysin-treated specimen (with a majority of non-mutant erythrocytes and reticulocytes lysed due to aerolysin) is subsequently analyzed. Even while the majority of erythrocytes and reticulocytes have been lysed, it is still possible to analyze $10^6$ or more "virtual reticulocytes" by setting the stop mode so that the proportionate number of beads (which are unaffected by aerolysin) have been interrogated. In this example, the stop mode would be set so that data accumulate until $10^6$ divided by 75 beads have been acquired, i.e., 13,333 beads. In this manner, it is possible to score the number of mutant reticulocytes per 13,333 beads, or in other words, per $10^6$ virtual reticulocytes.

Complement-mediated lysis of anti-CD55 or anti-CD59 antibody-labeled GPI+ cells can be carried out by standard techniques whereby cells are first incubated with antibody(s), and subsequently exposed to the extracellular factors that are involved in the Complement-mediated lysis cascade.

Of these techniques aimed at enhancing the rate by which mutant reticulocyte frequency measurements are determined, there are some practical advantages to the thresholding technique, as it simplifies the number of reagents and steps required to perform these measurements.

One significant use of the present invention relates to genotoxicity assessment. In this case, an exogenous test agent is applied over a range of doses or intensities to mammals of interest. This test agent exposure may occur one or several times as is the case in acute or subacute toxicity tests, or repeatedly as is the case in subchronic and chronic toxicity tests. The test agent may be a chemical or formulation, or it could be a physical entity, such as the energy. Chemicals which are known to damage DNA include, but are not limited to: inorganic genotoxicants (e.g., arsenic, cadmium and nickel), organic genotoxicants (especially those used as antineoplastic drugs, e.g., cyclophosphamide, cisplatin, cytosine arabinoside, etc.), anti-metabolites (e.g., 5-fluorouracil), organic genotoxicants that are generated by combustion processes (e.g., polycyclic aromatic hydrocarbons such as benzo(a)pyrene), as well as organic genotoxicants that are found in nature (e.g., aflatoxins such as aflatoxin B1). Examples of physical agents that are known to damage DNA include, but are not limited to: gamma radiation, beta radiation, and UV radiation.

After an appropriate length of expression time which allows mutated bone marrow progenitor cells to appear in peripheral blood as GPI-anchor deficient reticulocytes or erythrocytes (i.e., from several days to several weeks post exposure), blood is harvested and prepared for flow cytometric enumeration of pig-a mutants according to procedures outlined above and described in detail in the following examples.

Certain agents may offer protection from DNA damage, while others may magnify risk of damage. The present invention can also be used to evaluate the effects of an agent which can modify (i.e., enhance or suppress) such damage. To assess the suspected protective effects of an agent, mammals can be exposed to the putative protective agent either prior to, concurrently, or soon after exposure to a known genotoxicant. Any protective effect afforded by the agent can be measured relative to damage caused by the genotoxicant alone. Putative protective agents can be vitamins, bioflavonoids and anti-oxidants, dietary supplements (e.g., herbal supplements), or any other protective agent, whether naturally occurring or synthesized by man.

To assess the ability of an agent to synergistically or additively enhance genotoxicity, mammals can be exposed to the agent prior to, concurrently, or shortly after exposure to a known genotoxicant. Any additive or synergistic effect caused by the agent can be measured relative to damage caused by the genotoxicant alone.

The assays of the present invention can likewise be used to monitor chronic exposure to genotoxicant agents, for example, in individuals that work in environmental remediation, manufacturing industries that involve exposure to such agents, agricultural environments that involve pesticide or insecticide usage, etc. For these uses, period testing can be performed on a regular basis (e.g., weekly, monthly, quarterly, seasonally, biannually, etc.).

EXAMPLES

The examples below are intended to exemplify the practice of the present invention but are by no means intended to limit the scope thereof.

Example 1

Differential Labeling of Erythrocytes, Reticulocytes, Nucleated Cells, Platelets, and Mutant Erythrocytes In this example, a three-color procedure for differentially labeling and scoring pig-a cells is demonstrated.

Whole blood specimens (EDTA as anticoagulant) were obtained from the tail vein of vehicle- or ethyl-N-nitrosourea (ENU) treated rats (100 mg/kg/day for three days at 48 hr intervals; blood collected several weeks after the final administration). These specimens were centrifuged at low speed at least two times to significantly reduce the number of platelets. Thereafter, cells were contacted with anti-CD59-PE to differentially label mutant and non-mutant erythrocytes, and biotinylated anti-CD61 followed by streptavidin-Cy5-PE as a platelet-specific label used to exclude these particles from analysis. After washing steps to remove unbound antibodies and unbound streptavidin-Cy5-PE, cells were resuspended in a thiazole orange solution (0.1 µg/ml). Specimens were incubated at room temperature for about 30 minutes, and thereafter were placed on ice until flow cytometric analysis occurred (within about 4 hours).

As shown by FIGS. 3A-E, the labeling procedure was able to successfully discriminate mature erythrocytes and reticulocytes from other cell types, as well as from platelets. Furthermore, it was capable of providing high fluorescent resolution between CD59-negative and CD59-positive erythrocytes, thus facilitating quantification of mutant erythrocyte frequency.

Figure 3A:
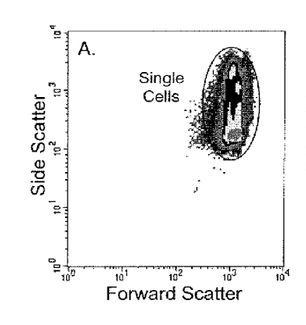
FIGS. 3A-E are bivariate graphs which illustrate the resolution achieved with a 3-color labeling procedure, and the gating strategy used to enumerate mutant and non-mutant erythrocytes.
Figure 3B:
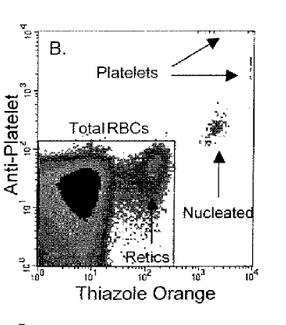
Figure 3C:
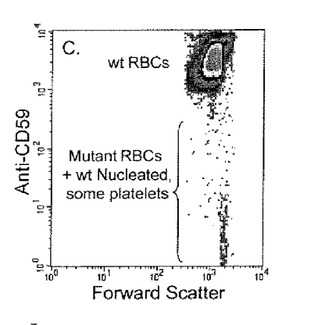
Figure 3D:
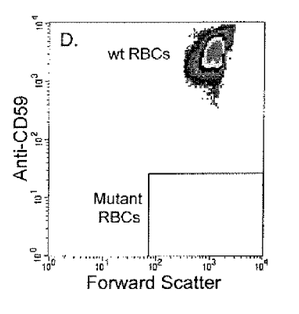
Figure 3E:
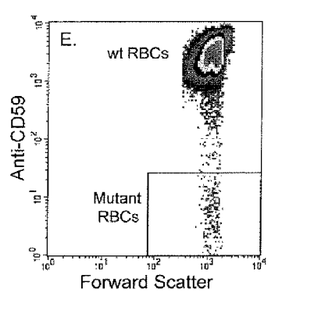

The flow cytometry data acquisition/analysis software (CellQuest v3.3) allowed for configuring alternative gating strategies. As shown in FIG. 3C, unless CD61-positive events (platelets) were excluded from analysis, mutant erythrocyte measurements suffered from spuriously high readings.

Example 2

Thresholding Technique Provides Rapid Assessment of Reticulocytes for pig-a Mutant Phenotype The thresholding technique is based on the fact that the vast majority of unfractionated blood cells are mature erythrocytes.

With appropriate staining (e.g., thiazole orange, SYTO® 13 dye, SYTO® 83 dye, SYTO® RNASelect™, or anti-CD71), it is possible to distinguish reticulocytes from their more mature counterparts.

In this case, it is possible to set the threshold parameter to the nucleic acid dye-associated fluorescence channel (e.g., FL1 for thiazole orange), as opposed to the more common forward scatter trigger. When set sufficiently high (that is, above the fluorescence intensity of mature erythrocytes), this can restrict analysis to reticulocytes.

Even so, fluorescence thresholding alone does not improve reticulocyte interrogation rates. Rather, it must be coupled with the preparation of very high density specimens. When these two adjustments are made, much quicker data acquisition rates are achieved. For instance, by eliminating mature erythrocytes with an FL1 threshold and analyzing specimens prepared at very high cell densities (for example $3 \times 10^8$/ml), it is possible to reduce the time needed to acquire $10^6$ reticulocytes from 80 minutes to about 5 to 15 minutes.

Figure 4A:
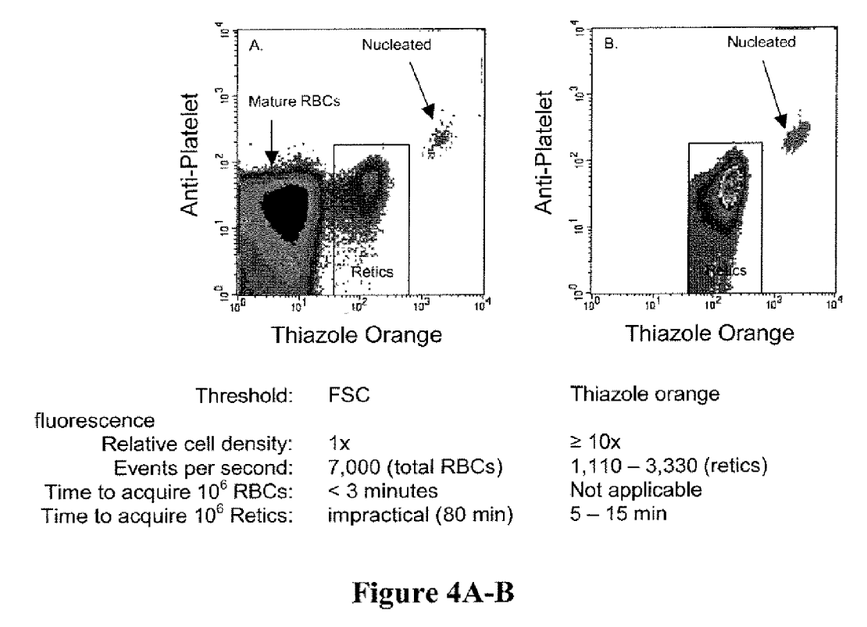

In practice, this means the mutation frequency for entire erythrocyte population and a mutation frequency for the reticulocyte fraction can each be efficiently determined by analyzing each stained blood specimen two times: once at high density with FL1 thresholding, and a second time upon dilution using a FSC threshold setting. In this manner it is possible to efficiently interrogate enough cells (e.g. $10^6$ reticulocytes and also $10^6$ total erythrocytes) for accurate measures of mutant frequency (see FIGS. 4A-B).

Example 3

Selective Lysis of Wild-Type Erythrocytes Enhances the Speed of Mutant Phenotype Scoring A second approach for enhancing the rate at which erythrocytes can be evaluated for the pig-a mutant phenotype is based on selective cell lysis.

To demonstrate this technique, female Sprague-Dawley rats were either untreated, or exposed to ENU at 100 mg/kg/day or 7,12-dimethyl-1,2-benz[a]anthracene (DMBA) at 40 mg/kg/day. Treatment occurred on three days (M, W, F), and tail vein blood was collected 6 weeks thereafter into EDTA-containing solutions. Blood cells were washed two times and are then stained with three fluorescent reagents according to the present invention. Specifically, specimens were contacted with anti-CD59-FITC to differentially label mutant and non-mutant erythrocytes, biotinylated anti-CD61 followed by streptavidin Cy5-PE as a platelet-specific label used to exclude these particles from analysis, and finally SYTO 83 dye to differentially stain mature erythrocytes, reticulocytes, and nucleated cells. Specimens were subsequently divided in order to provide pig-a mutant erythrocyte frequency measurements made with and without the use of aerolysin. These measurements were performed using "counting beads" as described in the Detailed Description of the Invention, and the results are presented in FIG. 5.

Figure 5:
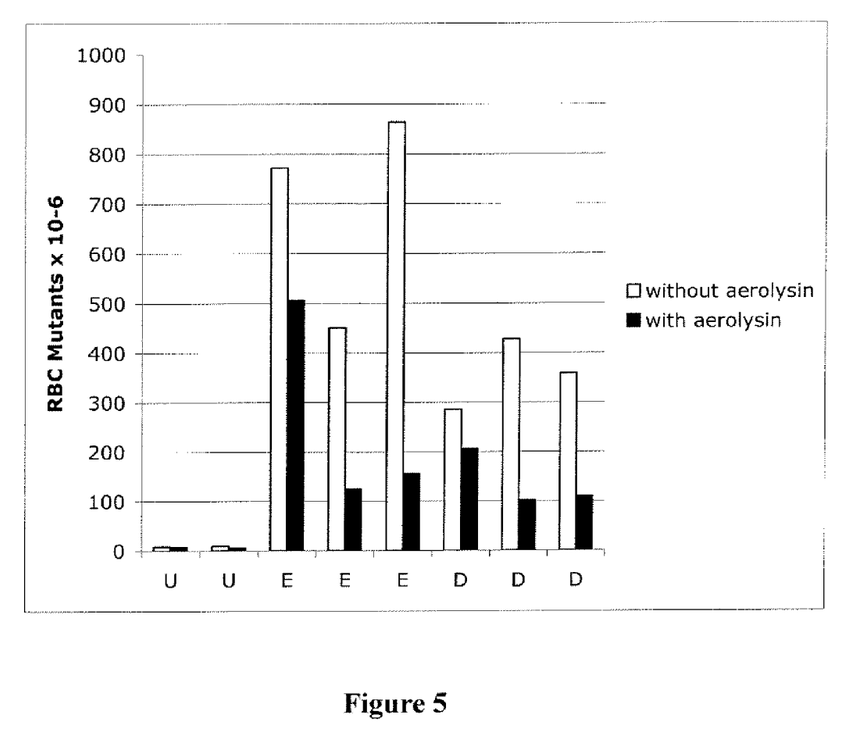
FIG. 5 is a graph of mutant erythrocyte (CD59-negative) frequency for untreated rats (U), ENU-treated rats (E) and DMBA-treated rats (D). Two values are presented for each individual, and correspond to analyses that did or did not utilize aerolysin to enrich for mutants. As these data illustrate, both techniques are able to demonstrate significant increases to CD59-negative cell frequencies for mutagen-exposed animals.

This and other experiments to date have demonstrated that mutagen-induced CD59-negative frequencies are somewhat lower when aerolysin is used to accomplish selective lysis. Even so, because spontaneous mutant frequencies have also tended to be somewhat lower, fold-increase values have only been moderately affected. Selective cell lysis with aerolysin therefore appears to represent one viable solution for enhancing throughput rates, although it is technically more challenging to execute relative to the thresholding technique described in Example 2 above.

Example 4

Influence of Blood Harvest Time

An experiment was performed to confirm that genotoxicant exposure would indeed increase the incidence of peripheral blood cells that exhibit a GPI-anchor deficiency. The use of serial blood specimens also facilitated an assessment of the influence of blood harvest time. For this experiment, Sprague Dawley rats were treated with either vehicle or 100 mg ENU/mg/day on three days (M, W, F). Blood was collected from the tail vein of these animals before treatment and over a 5 week post-exposure period. After two washing steps, high density blood samples were stained according to the present invention. Specifically, high density blood specimens were contacted with anti-CD59-PE to differentially label mutant and non-mutant erythrocytes, and biotinylated anti-CD61 followed by streptavidin-Cy5-PE as a platelet-specific label used to exclude these particles from analysis. After washing steps to remove unbound antibodies and streptavidin-Cy5-PE, cells were resuspended in a thiazole orange solution (0.1 µg/ml) and allowed to incubate at room temperature for about 30 minutes. Specimens were placed on ice and protected from light until flow cytometric analysis (within about 4 hours). Cells were analyzed according to the FL1 thresholding technique described in Example 2. Data are presented in FIG. 6.

Figure 6:
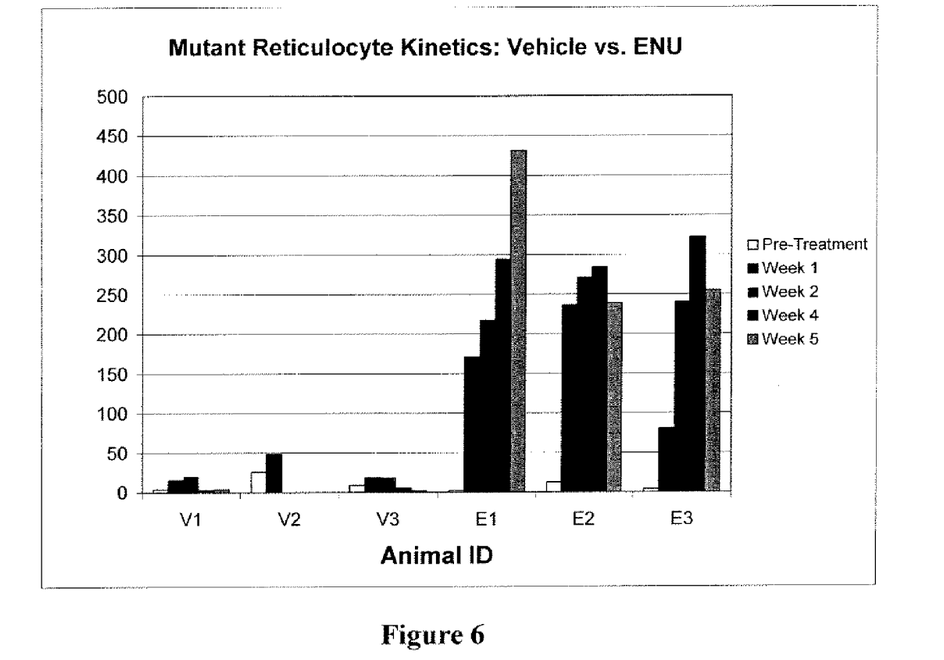
FIG. 6 is a graph of CD59$^-$ reticulocyte frequency graphed for each of three vehicle (V) and ENU (E) treated rats over a five week period. Mutation frequencies are greatly elevated for each of the treated animals. As predicted from the high rate of erythroblast division and differentiation into reticulocytes, significantly elevated frequencies are evident soon after treatment was initiated (week 1). For two of the three ENU-treated animals studied, a maximal response is evident by week 4.

These time-course data show markedly elevated mutant reticulocyte frequencies for each of the three ENU-treated animals studied. Importantly, significant changes over baseline values were observed quickly, that is, as soon as the one week time point. This was expected, give the rate at which erythroblasts divide and differentiate, thereby replacing the pool of pre-exposure reticulocytes. For animals E2 and E3, mutant frequency peaked at week 4. Animal E1's mutation frequency continued rise through week 5. This deviation from the other time courses cannot be explained at this time, but may reflect differences in dose deposition, metabolism, or other host-related factors that are not apparent from the limited population. Nevertheless, the data show a clearly evident effect of ENU on the treated rats.

Example 5

Mutant Erythrocytes Versus Mutant Reticulocytes

For this experiment, rats were untreated, or exposed to 100 mg ENU/kg/day or 40 mg DMBA/kg/day. These exposures were performed three times in one week (M, W, F). Blood was collected from the tail vein of these animals 4 weeks post-exposure. Blood samples were stained according to the present invention. Specifically, high density blood specimens were contacted with anti-CD59-PE to differentially label mutant and non-mutant erythrocytes, and biotinylated anti-CD61 followed by streptavidin-Cy5-PE as a platelet-specific label used to exclude these particles from analysis. After a washing steps to remove unbound antibodies and streptavidin-Cy5-PE, cells were resuspended in a thiazole orange solution (0.1 µg/ml) and allowed to incubate at room temperature for about 30 minutes. Specimens were placed on ice and protected from light until flow cytometric analysis (within about 4 hours). Cells were analyzed at low density with FSC thresholding, and also at high density with FL1 thresholding. As described in Example 2, this provided mutant frequencies in both the total erythrocyte and the reticulocyte populations. Data are presented in FIG. 7.

Figure 7:
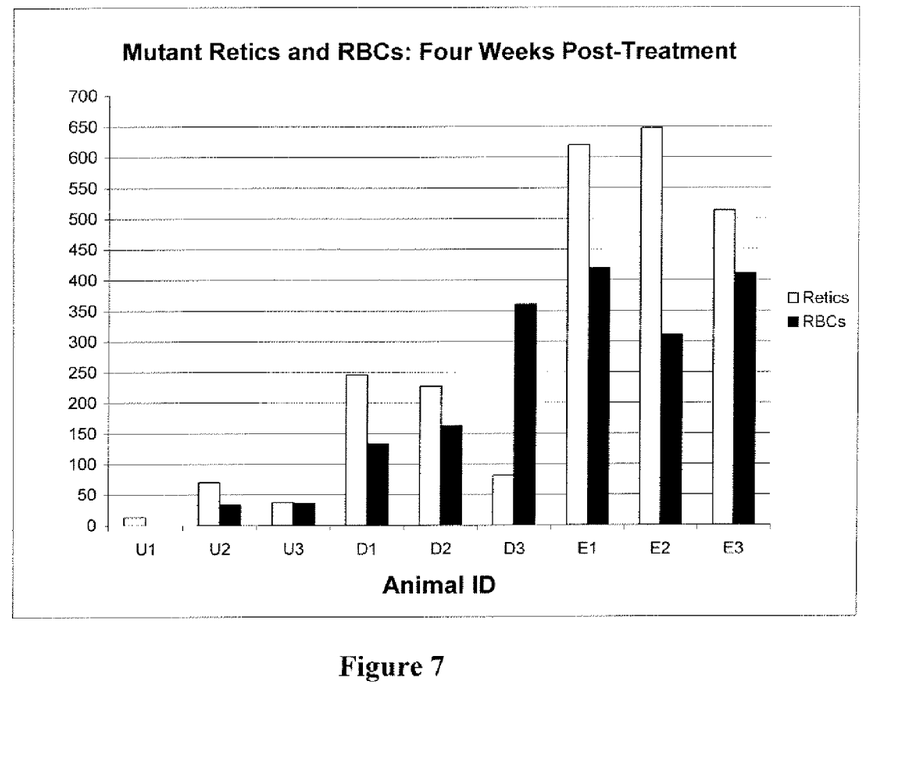
FIG. 7 graphs the frequency of CD59-negative reticulocytes (yellow bars) and CD59-negative erythrocytes (blue bars) at four weeks post-exposure for each of three untreated (U), DMBA (D) and ENU (E) treated rats. Mutation frequencies are greatly elevated in both the reticulocyte subpopulation and the total erythrocyte population for each of the treated animals. With one exception, the mutation frequency in the reticulocyte subpopulation is higher than the corresponding erythrocyte value.

The frequency of CD59⁻ cells in both the total erythrocyte pool as well as the reticulocyte subpopulation were highly elevated in all genotoxicant-treated animals. Note that the mutation frequency in the reticulocyte subpopulation was higher in 8 of 9 animals studied. One possible explanation is that the harvest time of 4 weeks post-exposure may more closely approximate the maximal response time-frame for the immature cohort compared to total erythrocytes. Alternately, if mutant erythrocytes exhibit a shortened life-span in circulation compared to their wild type counterparts, then this would tend to mute the response in the total erythrocyte population. In any case, both populations were shown to clearly reflect the effect of mutagen treatment when a sufficiently long period of expression time is provided. This provides support for measuring either or both erythrocyte populations when practicing the current invention. An overriding factor for many studies will likely be whether exposure occurred recently or not. In the case of a recent exposure, it is expected that analyses would benefit from reticulocyte-based mutation frequency measurements and not necessarily those based on total erythrocytes.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A kit for assessing the mutagenic DNA-damaging potential of an agent comprising:
   a first reagent that binds glycosylphosphatidylinositol (GPI1-anchor-expressing cells, but not GPI-anchor-deficient cells, and comprises a first fluorochrome;
   a second reagent that binds to mammalian platelets, and that comprises a second fluorochrome having a fluorescent emission spectrum that does not substantially overlap with a fluorescent emission spectrum of the first fluorochrome;
   a third fluorochrome-containing reagent that labels mature erythrocytes but not reticulocytes, the third fluorochrome having a fluorescent emission spectrum that does not substantially overlap with the fluorescent emission spectra of the first and second fluorochromes;
   optionally, one or more balanced salt solutions; and
   a computer readable storage medium comprising a cytometry data acquisition template that acquires from a flow cytometer scoring data for GPI-anchor-deficient erythrocytes and reticulocytes, which exhibit cell-specific forward- and side-scatter properties and the absence of fluorescence from the first reagent, and are distinguished from one another and from nucleated cells by fluorescence levels for the third reagent and distinguished from platelets that exhibit fluorescence of the second reagent as a basis to execute assessment of the mutagenic DNA-damaging potential of the agent.

2. The kit according to claim 1 wherein the first reagent is anti-CD59 antibody directly conjugated to the first fluorochrome, anti-CD55 antibody directly conjugated to the first fluorochrome, a non-lytic fluorescent aerolysin derivative, or a combination thereof.

3. The kit according to claim 1 wherein the second reagent is anti-CD42b antibody directly conjugated to the second fluorochrome, anti-CD61 antibody directly conjugated to the second fluorochrome, or a combination thereof.

4. The kit according to claim 1 wherein the third fluorochrome-containing reagent is a nucleic acid dye, an anti-CD71 antibody conjugated to the third fluorochrome, or the anti-CD71 antibody in combination with a secondary antibody conjugated to the third fluorochrome.

5. The kit according to claim 4 wherein the third fluorochrome-containing reagent is a cyanine nucleic acid dye.

6. The kit according to claim 1 further comprising one or more reagents that cause selective lysis of GPI-anchor-expressing cells.

7. The kit according to claim 6 wherein the one or more reagents that cause selective lysis comprise bacterial toxin aerolysin or a proaerolysin derivative.

8. The kit according to claim 6 wherein the one or more reagents that cause selective lysis comprise anti-CD55 or anti-CD59 antibodies in combination with one or more proteins that induce Complement-mediated lysis.

9. The kit according to claim 6 further comprising a suspension comprising microspheres.

10. The kit according to claim 1 further comprising instructions that provide cell handling procedures, and also mutant erythrocyte and/or mutant reticulocyte scoring via flow cytometry.

11. A kit for assessing the mutagenic DNA-damaging potential of an agent comprising:
    a first reagent that binds GPI-anchor-expressing cells, but not GPI-anchor-deficient cells, and comprises a first fluorochrome;
    a second reagent that labels mature erythrocytes but not reticulocytes, and comprises a second fluorochrome having a fluorescent emission spectrum that does not substantially overlap with the fluorescent emission spectrum of the first fluorochrome;
    instructions for handling cells, and using, the first reagent for labeling GPI-anchor-expressing cells and the second reagent for differentially labeling mature erythrocytes from reticulocytes and nucleated cells; and
    a computer readable storage medium comprising a cytometry data acquisition template that acquires from a flow cytometer scoring data for GPI-anchor-deficient erythrocytes and reticulocytes, which exhibit cell-specific forward- and side-scatter properties and the absence of fluorescence from the first reagent, and are distinguished from one another and from nucleated cells by fluorescence levels for the second reagent as a basis to execute assessment of the mutagenic DNA-damaging potential of the agent.

12. The kit according to claim 11, wherein the first reagent is anti-CD59 antibody directly conjugated to the first fluorochrome, anti-CD55 antibody directly conjugated to the first fluorochrome, a non-lytic fluorescent aerolysin derivative, or a combination thereof.

13. The kit according to claim 11 wherein the second reagent is a nucleic acid dye, an anti-CD71 antibody conjugated to the second fluorochrome, or the anti-CD71 antibody in combination with a secondary antibody conjugated to the second fluorochrome.

14. The kit according to claim 13 wherein the second reagent is a cyanine nucleic acid dye.

15. The kit according to claim 11 further comprising one or more reagents that cause selective lysis of GPI-anchor-expressing cells.

16. The kit according to claim 15 wherein the one or more reagents that cause selective lysis comprise bacterial toxin aerolysin or a proaerolysin derivative.

17. The kit according to claim 15 wherein the one or more reagents that cause selective lysis comprise anti-CD55 or anti-CD59 antibodies in combination with one or more proteins that induce Complement-mediated lysis.

18. The kit according to claim 15 further comprising a suspension comprising microspheres.

19. The kit according to claim 11 wherein said instructions include instructions for preparing a fractionated erythrocyte sample from a blood sample obtained from a mammal exposed to an agent that may induce mutagenic DNA damage.

20. The kit according to claim 11 further comprising one or more than one of (a)-(c) as follows:
 (a) one or more balanced salt solutions;
 (b) a suspension comprising microspheres; and
 (c) one or more reagents that cause selective lysis of GPI-anchor-expressing cells.

21. The kit according to claim 11 wherein the second reagent is a cyanine nucleic acid dye that is not thiazole orange.

* * * * *